US00PP18859P3

(12) United States Plant Patent
Layt

(10) Patent No.: US PP18,859 P3
(45) Date of Patent: May 27, 2008

(54) ***LOMANDRA FILIFORMIS* PLANT NAMED 'LMF500'**

(50) Latin Name: *Lomandra filiformis*
Varietal Denomination: LMF500

(75) Inventor: Todd Anthony Layt, New South Wales (AU)

(73) Assignee: Ozbreed Pty. Ltd., Richmond NSW (AU)

( * ) Notice: Subject to any disclaimer, the term of this patent is extended or adjusted under 35 U.S.C. 154(b) by 44 days.

(21) Appl. No.: 11/501,291

(22) Filed: Aug. 9, 2006

(65) Prior Publication Data

US 2007/0061934 P1 Mar. 15, 2007

Related U.S. Application Data

(60) Provisional application No. 60/711,323, filed on Aug. 25, 2005.

(51) Int. Cl.
*A01H 5/00* (2006.01)

(52) U.S. Cl. ..... Plt./384

(58) Field of Classification Search ..... Plt./384
See application file for complete search history.

(56) References Cited

PUBLICATIONS

Layt; "*Lomandra filifomis*'LMF500'" *Plant Varieties Journal* 17 (3): 23, 69 (Oct. 27, 2004).

*Primary Examiner*—Annette H Para
(74) *Attorney, Agent, or Firm*—Myers Bigel Sibley & Sajovec, P.A.

(57) ABSTRACT

'LMF500' is a distinctive variety of *Lomandra filiformis* characterized by a more compact growth habit with a greater shoot density than common *Lomandra filiformis*. In addition, 'LMF500' has a more glaucous leaf texture than common *Lomandra filiformis,* which results in an overall blue-green foliage colour, whereas common *Lomandra filiformis* has an overall grey-green to green foliage colour.

1 Drawing Sheet

Latin name of the genus and species: The Latin name of the novel variety disclosed herein is *Lomandra filiformis*.

Variety denomination: The inventive variety of *Lomandra filiformis* disclosed herein has been given the varietal denomination 'LMF500'.

BACKGROUND OF THE INVENTION

The present invention relates to a new and distinct perennial variety of *Lomandra filiformis,* which has been given the varietal denomination of 'LMF500'. Its market class is that of an ornamental grass-like plant. 'LMF500' is intended for use in landscaping and as a decorative grass-like plant.

Parentage. The *Lomandra filiformis* variety 'LMF500' was first discovered in 1999 in an Australian nursery in the state of New South Wales during a routine inspection of large quantities of common *Lomandra filiformis* production stock. 'LMF500' is a seedling selection from common *Lomandra filiformis*. 'LMF500' was selected due to its very glaucous upper side leaf texture.

Asexual reproduction. 'LMF500' was first propagated asexually by division in the state of New South Wales, Australia and has since been asexually propagated by division and micropropagation.

Divisions were made for several subsequent generations, and 'LMF500' was observed to retain the characteristics that were noted in the original 'LMF500' seedling. Thus, the distinctive characteristics of the inventive 'LMF500' variety have remained stable and true to type from generation to generation through successive cycles of asexual reproduction.

An application for plant breeders' rights for variety 'LMF500' has been filed with the Australian Plant Breeders' Rights Office, and was first gazetted in the Plant Varieties Journal under Application No. 2004/249.

SUMMARY OF THE INVENTION

'LMF500' is a distinctive variety of *Lomandra filiformis* characterized by a more compact growth habit with a greater shoot density than common *Lomandra filiformis*. In addition, 'LMF500' has a more glaucous leaf texture than common *Lomandra filiformis,* which results in an overall blue-green foliage colour, whereas common *Lomandra filiformis* has an overall grey-green to green foliage colour.

BRIEF DESCRIPTION OF THE FIGURE

The photograph in the drawing was made using conventional techniques and shows the colors as true as reasonably possible by conventional photography. Colors in the photograph may differ slightly from the color values cited in the detailed botanical description, which accurately describe the colors of the new *Lomandra filiformis*.

BOTANICAL DESCRIPTION OF THE PLANT

Figure 1:
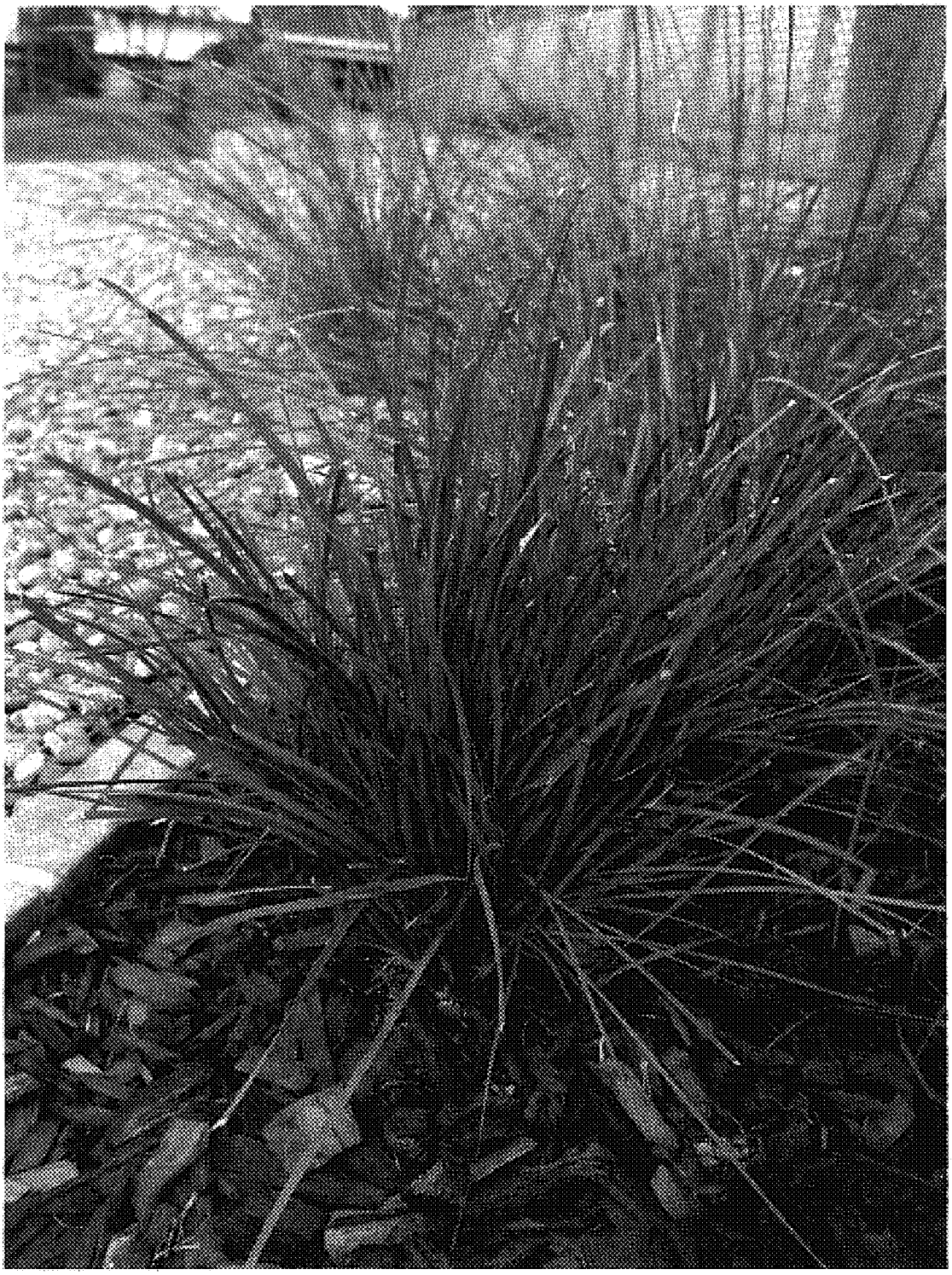
FIG. 1 shows an exemplary 2 year old 'LMF500' plant.

The following is a detailed botanical description of a new and distinct variety of a *Lomandra filiformis* ornamental grass-like plant known as 'LMF500'. Plant observations were made on 18 month old plants grown in New South Wales, Australia. Unless indicated otherwise, the descriptions disclosed herein are based upon observations made of mature 'LMF500' plants grown in nursery pots and field plots.

Those skilled in the art will appreciate that certain characteristics will vary with older or, conversely, younger plants. 'LMF500' has not been observed under all possible environmental conditions. Where dimensions, sizes, colours and other characteristics are given, it is to be understood that such characteristics are approximations or averages set forth as accurately as practicable. The phenotype of the variety may differ with variations in the environment such as season, temperature, light intensity, day length, cultural conditions and the like. Colour notations are based on The Royal Horticultural Society Colour Chart (The Royal Horticultural Society, London, 1995 edition).

'LMF500' is a perennial, dioecious, *Lomandra filiformis* plant which is a seedling selection from common *Lomandra filiformis*. After its selection, 'LMF500' was asexually propagated by division. 'LMF500' has an overall foliage colour that appears to be blue-green due to a very glaucous leaf texture. This foliage colour is unusual for *Lomandra filiformis* plants, which usually have weak leaf glaucosity and an overall foliage colour of grey-green to green. 'LMF500' also has a more compact growth habit and greater shoot density as compared with common *Lomandra filiformis*. A botanical description of 'LMF500' and a comparison with other varieties of *Lomandra filiformis* are provided below. A representative 'LMF500' plant is shown in FIG. 1.

TECHNICALDESCRIPTION OF THE VARIETY

Growth habit: 'LMF500' is a short, rhizomatous plant forming a compact tussock. Average plant height is 26 cm and average plant spread is 22 cm in a mature plant grown in a 140 mm nursery pot or a field plot in Sydney, New South Wales, Australia.

Foliage: The upper and lower side of the leaf is yellow-green (RHS 147A) in colour with the wax layer removed. The leaf texture is strongly glaucous resulting in an overall bluish-green foliar colour approximating greyed-green (RHS 189A–B). The leaf is generally 3–4 mm in width, and reaches an average length of 22 mm. The leaf base is cauline, leaf margin is entire, leaf apex is dentate and leaf surface texture is glaucous. The leaf venation pattern is parallel and the venation colour is the same as the rest of the leaf (yellow-green, RHS 147A). The leaf basal sheaths are brown in colour (RHS 200A). The leaf is generally a uniform width from base to the tip, margins shred at the base to a greyed-orange colour (RHS 165A), with a dentate apex typical of *Lomandra filiformis*.

Roots: The roots of 'LMF500' are fibrous and spreading, similar to other *Lomandra filiformis*.

Rhizomes: Very short (3 cm to 4 cm); rhizome colour with the leaf sheath removed is white (RHS 155C); surface texture of the rhizome is smooth.

Bud: Bud shape is oval.

Inflorescence: The inflorescence is a spike (a panicle of clusters), composed of male flowers. The predominant colour of the inflorescence at anthesis is yellow (RHS 6A), with a short length of 50–60 mm and an average width of 20 mm.

Floret length: The average length of the floret is 3 mm.

Pedicels: Absent; the florets are sessile.

Bracts: Average bract length is 6 mm; bract colour is greyed-brown (approximately RHS 199D).

Flowers: Colour of outer perianth is greyed-purple (RHS 183C) proximally, yellow-green (RHS 146A–B) distally along the central zone, and greyed-yellow (RHS 161D) along each perianth segment margin; the colour of inner perianth is yellow (RHS 6A) fading toward the margin to yellow (RHS 13D).

Flower rachis: The length of the flower rachis is 30–40 mm.

Reproductive organs of male florets: Six stamens; anther size is 0.5 mm to 0.8 mm in length; anther colour is yellow (approximately RHS 8B).

Seed: Flowers are male; seed is not produced.

Flowering period: The primary flowering period is late winter to spring with secondary flowering occurring in summer to autumn in Sydney, New South Wales, Australia.

Lastingness of bloom: Approximately 9 days in summer in Sydney, New South Wales, Australia.

Fragrance: Fragrance is typical of the species and of medium strength.

Environmental tolerances: 'LMF500' has shown the potential for shade tolerance and further shade tolerance tests are underway. 'LMF500' has been observed to hold colour to −8 degrees Celsius without any noticeable change in appearance of the plant. With testing at −12 degrees Celsius, minor frost burning was observed at the tips of the leaves, with slight paling in colour. 'LMF500' has excellent drought tolerance. After severe wilting, 'LMF500' has been noted to recover with watering. 'LMF500' does well in sandy soils, but also tolerates heavy, clay-type soils well.

Disease resistance: 'LMF500' has good resistance to root rot comparable with most other *Lomandra filiformis*.

These features and other characteristics of the plant are apparent from the figure.

Comparison of 'LMF500' with Other Varieties of *Lomandra filiformis*

'LMF500' has a more dense growth habit with shorter internodes than common *Lomandra filiformis* and another comparable type of *Lomandra filiformis,* known as 'Mondra' (unpatented), resulting in an absence or very weak expression of canes at the shoot base. 'LMF500' has a taller plant height than 'Mondra'. The flower spike of 'LMF500' is small, which is typical of *Lomandra filiformis*.

In addition, 'LMF500' has a more glaucous leaf texture than common *Lomandra filiformis* and 'Mondra', which results in an overall bluish-green foliage colour, whereas common *Lomandra filiformis* has an overall grey-green to green foliage colour and 'Mondra' has weaker glaucosity and an overall yellow-green foliage colour. When the glaucous waxy layer is removed from the leaf, 'LMF500' has a leaf colour that is yellow-green (RHS 147A) compared to the common *Lomandra filiformis* yellow-green (RHS 146A). The combination of its compact form and glaucous leaf texture makes 'LMF500' an attractive ornamental grass-like plant.

That which is claimed is:

1. A new and distinct variety of *Lomandra filiformis* plant named 'LMF500', substantially as described and illustrated herein.

* * * * *